United States Patent [19]
Ofstead

[11] 3,935,179
[45] Jan. 27, 1976

[54] CYCLOOLEFIN METATHESIS
[75] Inventor: Eilert A. Ofstead, Cuyahoga Falls, Ohio
[73] Assignee: The Goodyear Tire & Rubber Company, Akron, Ohio
[22] Filed: Apr. 1, 1974
[21] Appl. No.: 456,912

[52] U.S. Cl. ........ 260/93.1; 252/429 B; 260/88.2 B; 260/683 D
[51] Int. Cl.² ........................................... C08F 4/22
[58] Field of Search ..................... 260/88.2 B, 93.1; 450/665.5

[56] References Cited
UNITED STATES PATENTS
3,449,310  6/1969  Dall'Asta et al. .................. 260/93.1
3,631,010  12/1971  Witte et al. ......................... 260/82.1

*Primary Examiner*—Stanford M. Levin
*Attorney, Agent, or Firm*—F. W. Brunner; J. Y. Clowney

[57] ABSTRACT

There is disclosed a new process for ring-opening polymerization of cycloolefins by the use of a catalyst comprising (A) tungsten or molybdenum halides, (B) alkyl aluminum halides and (C) an alcohol which may optionally contain a halogen substituent and (D) an alcohol which has a nitrile substituent. Also the catalyst is disclosed as useful in metathesis of olefins.

7 Claims, No Drawings

CYCLOOLEFIN METATHESIS

This invention is directed to a process for the ring-opening polymerization of unsaturated alicyclic hydrocarbons. It is also directed to novel catalyst systems useful for this ring-opening polymerization process. These catalyst systems are further useful for the interconversion of acyclic olefins according to the method known as the olefin metathesis reaction (also called the olefin dismutation or olefin disproportionation reaction).

The olefin metathesis reaction is a unique bond-reorganization process, whereby materials possessing carbon-to-carbon double bonds, undergo a redistribution of constituents as depicted in the following equations:

$$2R_1CH = CHR_2 \rightleftarrows R_1CH = CHR_1 + R_2CH = CHR_2$$

The olefin metathesis reaction, being an equilibrium process, facilitates: (1) obtaining the olefins $R_1CH = CHR_1$ and $R_2CH = CHR_2$ starting from $R_1CH = CHR_2$; or alternatively, (2) obtaining the olefin $R_1CH = CHR_2$ by starting from a mixture of olefins $R_1CH = CHR_1$ and $R_2CH = CHR_2$.

Similarly, the ring-opening polymerization reaction of cycloolefins also involves the scission of the carbon-to-carbon double bonds in the cycloolefin ring. The alkylidene carbons are rejoined to other such carbons derived from other monomer units to form the linear unsaturated polymer chain. Thus, the ring-opening of cyclopentene, for instance, yields a repeat unit:

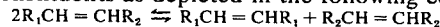

This repeat unit has also been expressed in the following equivalent forms:

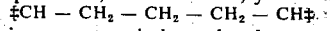

and

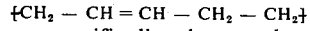

More specifically, the novelty of the present invention relates to the use of nitrile-substituted hydroxy compounds employed as catalyst modifiers for transition-metal/aluminum alkyl halide catalyzed ring-opening polymerizations. These modifiers can be used to produce catalyst systems which exhibit excellent activity as cycloolefin ring-opening polymerization catalysts. As a result, it is possible to use short reaction times and mild polymerization temperatures. Furthermore, very low catalyst concentrations may be used with excellent results. Thus, good yields of product can be obtained when the molar ratio of transition metal:monomer is as low as 1:20,000 or less.

The process of this invention comprises the ring-opening polymerization or copolymerization of at least one unsaturated alicyclic compound selected from the group consisting of (1) unsaturated alicyclic compounds containing four or five carbon atoms and one double bond in the ring, (2) non-conjugated, unsaturated alicyclic compounds containing at least seven carbon atoms in the ring and at least one double bond in the ring, and (3) polycyclic olefins and diolefins by subjecting said alicyclic compounds or their mixture to polymerization conditions in the presence of a catalyst system comprising (A) a transition metal salt selected from the group consisting of tungsten halides and oxyhalide and molybdenum halides and oxyhalides, (B) at least one compound selected from the group consisting of dialkylaluminum halides, alkylaluminum sesquihalides and alkylaluminum dihalides, (C) at least one hydroxy compound of the general formula ROH wherein R is selected from the group consisting of alkyl and cycloalkyl and wherein R contains a nitrile substituent, and (D) a hydroxy compound of the general formula R'OH wherein R' is selected from the group consisting of alkyl, cycloalkyl, aralkyl, alkoxyalkyl, haloalkyl and aryl, wherein the molar ratio of A:B:C:D lies within the range of 1:0.5–10:0.5–3:0.5–2.

The desired polymerization of alicyclic olefins results in linear, unsaturated polymers having repeating units derived from the opening the ring of the unsaturated alicyclic compounds.

It is known that the catalysts useful for this process facilitates the cleavage of carbon-to-carbon double bonds. The resulting halves of molecules, designated alkylidenes fragments, then recombine to give the new olefin products.

The polymerization catalysts of this invention may be employed to prepare a wide variety of useful polymers having different properties depending upon the particular monomer or combination of monomers chosen to be polymerized, the particular catalyst combination employed and the particular polymerization condition employed. The linear, unsaturated products resulting from the use of the polymerization catalysts of this invention can be employed in a variety of applications, for example, they may be employed to produce finished rubber articles such as pneumatic tires, molded goods and the like or these materials may be useful in coatings in adhesives or in the manufacture of articles such as films and fibers.

Representative but not restrictive of the unsaturated alicyclic monomers described in (1) above are cyclobutene, 3-methylcyclobutene, cyclopentene and 4-methylcyclopentene. Representative of the monomers described in (2) above are cyclopentene, cyclooctene, cyclodecene, cyclododecane, 1,5-cyclooctadiene, 1,9-cyclohexadecadiene, 1,5,9-cyclododecatriene, 3-methylcyclooctene, 3-phenylcyclooctene, 1-methyl-5-cyclooctadiene, 1-chloro-1,5-cyclooctadiene, 1,2-dimethyl-1,5-cyclooctadiene, and the like.

Representative of polycyclic olefins and diolefins described in (3) above are 3,3'-bicyclopentene,

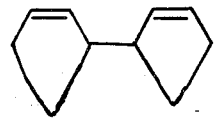

3,3'-bicyclooctene,

bicyclo[4,3,0]nona-3,7-diene,

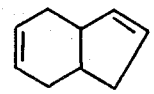

dicyclopentadiene, norbornadiene, norbornene, 5-vinylnorbornene, 5-alkylnorbornene and tricyclo[8,2,1,0$^{2,9}$]trideca-5,11-diene.

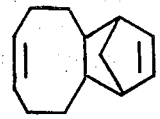

Representative of the organometallic catalyst components in (B) above are diethylaluminum chloride, diisobutyl aluminumchloride, diethylaluminum fluoride, dipropylaluminum bromide, ethylaluminum sesquichloride, methylaluminum sesquibromide, butylaluminum sesquichloride, ethylaluminum dichloride, propylaluminum dichloride, isobutylaluminum dibromide and the like. Of these, it is usually preferred to employ organoaluminum chlorides.

Representative of the compounds useful as the (C) catalyst component of the present invention include 2-hydroxypropionitrile (also known as hydracylonitrile), 2-hydroxy-2-methylpropionitrile, 2-hydroxycyclopentylnitrile, 2-hydroxycyclohexylnitrile, 3-chloro-2-hydroxybutyronitrile, 1-chloro-2-hydroxypropionitrile and the like.

Generally, it is preferred to use a nitrile-substituted hydroxy compound wherein the nitrile group is situated on the carbon atoms adjacent to the carbon atoms bearing the hydroxy group, as in the representative examples given above. On the other hand, when the nitrile group is situated on that carbon atom which bears the hydroxy group, as in the cyanohydrins of aldehydes and ketones, or when the nitrile group is more remote from the hydroxy group, as in 3-hydroxybutyronitrile, 4-hydroxyvaleronitrile and the like, the resulting catalyst combinations generally exhibit a lesser degree of activity for the ring-opening polymerization process, although many catalyst combinations involving modifiers such as these, nevertheless exhibit a significant level of activity.

It has been found that the preferred nitrile-substituted hydroxy compounds of this invention can be utilized very effectively with a wide variety of other types of hydroxy compounds, designated R'OH above. Many of these latter hydroxy compounds when used alone as catalyst modifiers, afford catalyst systems which exhibit some degree of activity for cycloolefin polymerization. However, the activity of these systems can be significantly enhanced when they are in combinations with the preferred nitrile-substituted modifiers of this invention.

As stated above, a wide variety of types of hydroxy compounds (R'OH) can be utilized as comodifiers in combinations with nitrile-substituted modifiers. These R'OH compounds include alkyl and cycloalkyl alcohols which may be substituted by halogen, alkoxy or ary substituents, phenols, halo-substituted phenols and the like.

Very active catalyst combinations may also be obtained when nitrile-substituted hydroxy compounds of the present invention are employed as the sole catalyst modifiers. That is to say, it is not essential that hydroxy compounds of the type designated R'OH above be employed in the practice of this invention in order to obtain catalysts having good activity for the polymerization of cycloolefins.

Representative of the transition metal salts of (A) are tungsten hexachloride, tungsten hexabromide, tungsten oxytetrachloride, tungsten oxytetrabromide, tungsten hexafluoride and the like.

Representative of alcohols described as R'OH in (D) are the simple aliphatic alcohols such as ethyl, propyl and butyl alcohols, cyclopentanol, cyclohexanol, phenol chloropropyl alcohol, chloroethanol glycol, chlorophenol and the like.

The catalyst system set forth above are prepared by mixing the components by known technique. Thus, the catalyst systems may be prepared by "preformed" or "in situ" techniques, or by a combination of these techniques. By the preformed method, the catalyst components are mixed together prior to exposure to any of these components to the alicyclic monomers to be polymerized. In the "in situ" method, the catalyst components are added individually to the alicyclic monomers. In the handling and transfer of the catalyst components, it is often convenient to utilize solutions of these components in suitable inert solvents such as benzene, toluene, chlorobenzene, hexane, pentane and the like.

The order of addition of the catalyst components to each other is of interest in the practice of this invention.

When the in situ method is employed, solely, it is much preferred to add the B component last, but the particular order of the A, C and D components is generally not critical. Combination of in situ and preformed methods can also be used effectively. In this case, it is generally preferred to employ the B component according to the in situ method, but component A may be preformed with component C or D or with both C and D. However, if either the C or the D component is to be used according to the in situ method, then it is preferred that the B component be the last one to be added.

It has been found that when the preformed technique is employed with the catalyst components A, C and D, some aging of the mixture of the components is desirable. During this aging period, color changes are usually observed. This aging period may require only a few minutes, or it may take several hours. The aging process can be carried out at ambient temperature in the range of 20°–25°C, or it may be accelerated by the use of moderately elevated temperatures in the range of 30°–100°C. It has also been found to be advantageous to remove some of the hydrogen chloride which is formed as a by product when the preformed method is used.

Known techniques may be used for removal of this hydrogen chloride. These techniques include the use of a stream of an inert gas which can be bubbled through the catalyst solution, or the use of a vacuum, to withdraw vapors of hydrogen chloride.

The amount of catalyst employed in the practice of this invention may range over a wide concentration range. Of course, a catalytic amount of the catalyst must be employed but the optimum amount depends upon a number of factors such as the temperature employed, the particular alicyclic monomers employed, the purity of the reaction conditions employed, the reaction time desired and the like. Generally, it is preferred to use at least about 0.01 parts by weight of the A component per 100 parts by weight of the alicyclic monomer or mixture of monomers.

The operating conditions which are employed in the process of this invention may vary. The polymerization may be carried out in solution or in bulk. When solvents or diluents are employed, they should be chosen so as not to adversely affect the desired polymerization process. Representative examples of useful solvents are liquid aromatic hydrocarbons such as benzene, toluene and chlorobenzene, aliphatic saturated hydrocarbons such as pentane, hexane, petroleum ether and decane, and alicyclic saturated hydrocarbons such as cyclopentane, cyclohexane, decalin and the like.

Temperature at which the polymerization can be carried out can be varied over a wide range. It is generally preferred to conduct these polymerizations under relatively mild reaction conditions over the range of about −20°C to about 100°C.

The polymerization times will vary and can range from less than a minute to 24 hours or more depending upon the polymerization conditions and the extent of polymerization desired. Generally, however, a satisfactory polymerization product is obtained in a matter of only a few minutes or hours.

The polymerization reaction may be carried out as a batch or as a continuous process. In performing the polymerization of this invention, the introduction of the monomer, catalyst and solvent, when a solvent is employed, can each be made to the reaction zone intermittently and/or continuously.

The practice of this invention is further illustrated by reference to the following examples, which are intended to be representative rather than restrictive of the scope of this invention. All experiments were conducted in an atmosphere of dry nitrogen.

EXAMPLE I changing premix and catalyst components were conducted under a nitrogen atmosphere. The order of catalyst addition to the polymerization bottles containing premix was tungsten component, followed by the organoaluminum component.

In each of the experiments shown in Table 1, 0.40 ml of the solution of the tungsten component was employed, which corresponded to a molar ratio of cyclopentane/w of about 5000/1. Polymerizations were terminated with a small amount of isopropanol, and the resulting solutions were dried under vacuum. Inherent viscosities were determined by benzene at 30°C. The percent trans values were determined by a method described in Journal of Polymer Science; Polymer Physics Edition; Vol. 11, page 529 (1973) published by John Wiley and Sons, Inc.

Experiments 10 and 11 are comparison tests which show that nitrile-substituted alcohols in which the nitrile is not situated on the carbon adjacent to that bearing the hydroxy group are much less effective as cocatalysts. Experiments 12 and 13 are comparison tests which show that when the nitrile-substitutent is not substituted on the hydroxy compound, the effectiveness of the cocatalyst is not significantly increased.

Table 1

| Exp No. | ROH | Molar Ratio, ROH/WCl$_6$ | EADC, Moles×10$^5$ | DEAC, Moles×10$^5$ | CP conc, wt. % | Polym Time, Min. | Percent Conv. | Inh Visc. | Percent Trans | Appearance |
|---|---|---|---|---|---|---|---|---|---|---|
| 1 | N≡CCH$_2$CH$_2$OH | 1 | 6 | — | 18.0 | 60 | 63.0 | 5.47 | 91 | rubbery solid |
| 2 | N≡CCH$_2$CH$_2$OH | 2 | 3 | — | 18.0 | 60 | 54.1 | 8.51 | — | " |
| 3 | N≡CCH$_2$CH$_2$OH | 2 | 4 | — | 18.0 | 60 | 75.6 | 5.02 | 92 | " |
| 4 | N≡CCH$_2$CH$_2$OH | 3 | 8 | — | 18.0 | 60 | 77.0 | 3.51 | — | " |
| 5 | ClCH$_2$CH(OH)CH$_2$C≡N | 2 | 8 | — | 19.9 | 100 | 76.0 | 3.42 | — | " |
| 6 | 2-hydroxycyclopentanenitrile$^b$ | 1 | 8 | — | 19.0 | 120 | 70.3 | — | 86 | " |
| 7 | 2-hydroxycyclopentanenitrile$^b$ | 2 | 12 | — | 19.0 | 70 | 53.5 | — | 86 | " |
| 8 | N≡CCH$_2$CH$_2$OH | 2 | — | 6 | 19.8 | 60 | 17.3 | 7.60 | — | " |
| 9 | — | 0 | 6 | — | 18.0 | 60 | 1.3 | — | — | — |
| 10 | (CH$_3$)$_2$C(OH)C≡N | 1 | 6 | — | 21.6 | 90 | 8.9 | — | — | — |
| 11 | N≡C(CH$_2$)$_6$OH | 2 | 8 | — | 19.0 | 70 | 13.4 | — | 76 | — |
| 12 | CH$_3$CH$_2$OH | 2 | 8 | — | 21.1 | 120 | 19.9˙ | — | — | — |
| 13$^a$ | CH$_3$CH$_2$OH | 2 | 6 | — | 17.7 | 60 | 17.7 | — | — | — |

$^a$CH$_3$C≡N was added to the WCl$_6$ solution with the CH$_3$CH$_2$OH during the preforming step; molar ratio CH$_3$C≡N/WCl$_6$ = 2/1.
$^b$2-hydroxycyclopentanenitrile used in 6 and 7.

The preformed technique was employed to prepare solutions of WCl$_6$ modified with the various hydroxy compounds designated in Table 1. The required amount of the hydroxy compound was added to an 0.05 molar solution of WCl$_6$ in dry benzene and allowed to react for about 24 hours at about 23°C. These solutions were then flushed with dry nitrogen to expel free HCl prior to being used. Ethyl-aluminum dichloride (EADC) or diethylaluminum chloride (DEAC) were employed as 0.20 molar solutions in benzene. Polymerizations.

A series of ring-opening polymerizations was carried out using solutions of freshly-distilled cyclopentene (CP) in benzene. These premix solutions were further purified by being passed through a mixture of silica gel and alumina before being charged to reaction bottles. Polymerizations were undiluted with 40 ml. of premix in 4-oz. glass bottles kept at 0°C. All manipulations of

EXAMPLE II

A series of polymerizations was carried out similar to those in Example I, except that nitrile-substituted hydroxy compounds (ROH) were employed in combinations with other hydroxy compounds R'OH which did not bear a nitrile substituent. The preformed technique was employed to prepare solutions of WCl$_6$ and the hydroxy compounds. For these experiments, the ROH component was first added to an 0.05 molar solution of WCl$_6$ in benzene and allowed to react for about 1 hour at 23°C. The resulting solution was flushed with dry N$_2$ to expel HCl, and the R'OH component was then added and allowed to react for about 24 hours at about 24°C and the solution was again flushed with dry N$_2$. All other details of the experimental procedure were similar to those given in Example I.

TABLE 2

| Exp No. | R'OH | Molar ratio R'OH/WCl$_6$ | ROH | Molar ratio ROH/WCl$_6$ | EADC, Moles×10$^5$ | CP conc, Wt % | Polym Time, Min. | Percent Conv | Inh Visc | Percent Trans |
|---|---|---|---|---|---|---|---|---|---|---|
| 14 | CH$_3$CH$_2$OH | 1 | N≡CCH$_2$CH$_2$OH | 1 | 4 | 18.0 | 60 | 75.8 | 3.34 | 86 |

TABLE 2-continued

| Exp No. | R'OH | Molar ratio R'OH/WCl$_6$ | ROH | Molar ratio ROH/WCl$_6$ | EADC, Moles×10$^5$ | CP conc, Wt % | Polym Time, Min. | Percent Conv | Inh Visc | Percent Trans |
|---|---|---|---|---|---|---|---|---|---|---|
| 15 | ClCH$_2$CH$_2$OH | 1 | N≡CCH$_2$CH$_2$OH | 1 | 6 | 19.3 | 90 | 76.4 | 3.19 | 85 |
| 16 | ClCH$_2$CH$_2$OH | 1 | ClCH$_2$CH(OH)CH$_2$C≡N | 1 | 6 | 19.0 | 70 | 77.6 | — | — |
| 17 | CH$_3$CH$_2$OCH$_2$CH$_2$OH | 1 | N≡CCH$_2$CH$_2$OH | 1 | 6 | 18.4 | 150 | 77.0 | — | — |
| 18 | CH$_3$CH$_2$OCH$_2$CH$_2$OH | 2 | — | — | 6 | 18.4 | 150 | 6.0 | — | — |

EXAMPLE III

A series of experiments was carried out similar to Example II, except that hexane was used in place of benzene for the preparation of the premix solution. The CP concentration was 22.0 percent by weight, 6×10$^{-5}$ moles of EADC was employed as the cocatalyst and the polymerization time was 90 minutes.

TABLE 3

| Exp No. | R'OH | Molar ratio R'OH/WCl$_6$ | ROH | Molar ratio ROH/WCl$_6$ | Perc Conv | Appearance |
|---|---|---|---|---|---|---|
| 19 | ClCH$_2$CH$_2$OH | 1 | N≡CCH$_2$CH$_2$OH | 1 | 60.4 | Rubbery solid |
| 20 | ClCH$_2$CH$_2$OH | 1 | (CH$_3$)$_2$C(OH)CH$_2$C≡N | 1 | 23.8 | " |

EXAMPLE IV

Two polymerizations were carried out in order to illustrate the effectiveness of nitrile-substituted modifiers when very low amounts of catalyst are employed.

A polymerization was carried out similar to Experiment 2 in Example I, except that 0.20 ml of the tungsten catalyst solution was employed instead of 0.40 ml. The molar ratio of CP/W was about 9/200/1. A yield of 73.0 percent was obtained of a strong rubbery solid having an inherent viscosity of 4.69.

A polymerization was carried out similar to Experiment 14 in Example II, except the initial concentration of CP was 19.5 percent by weight, the polymerization time was 90 minutes and 0.10 ml of the tungsten catalyst solution was employed instead of 0.40 ml. The molar ratio of CP/W was about 19,800/1. A yield of 79.2 percent was obtained of a strong, rubbery solid having an inherent viscosity of 5.04.

EXAMPLE V

A polymerization of CP was conducted similar to Experiment 3 of Example I except that the in situ technique was employed to modify the WCl$_6$. Thus, 0.40 ml of an 0.05 molar solution of WXl$_6$ in benzene was introduced into 40 ml of a 20.4 wt-% solution of CP in benzene containing 4×10$^{-5}$ moles of 2-hydroxypropanenitrile, followed by 0.40 ml of a 0.20 molar solution of EADC. The yield was 81.2 percent of a rubbery polymer having an inherent viscosity of 2.30.

EXAMPLE VI

Two polymerizations of CP were conducted similar to those of Example II except that the WCl$_6$ was modified by a combination of the preformed and in situ techniques. An 0.05 molar preformed solution of WCl$_6$ and 2hydroxypropanenitrile (molar ratio 1/1) was prepared according to the procedure given in Example I, and 0.40 ml of this solution was introduced into 40 ml of a 21.4 weight percent solution of CP in benzene containing 2×10$^{+5}$ moles of 2,4,6-trichlorophenol followed by 0.30 ml of an 0.20 molar solution of EADC. The polymerization was terminated after 120 minutes to give a yield of 80.6 percent of rubbery polymer having an inherent viscosity of 2.87.

To 40 ml of a 19.2 wt percent solution of CP in benzene containing 2×10$^{-5}$ moles of 3-hydroxypropanenitrile was added 0.40 ml of a 0.05 molar preformed solution of WCl$_6$ and 2-chloroethanol followed by 0.30 ml of an 0.20 molar solution of EADC. Polymerization was terminated after 90 minutes to give a 74.2 percent yield of a rubbery polymer having an inherent viscosity of 2.85.

EXAMPLE VII

To 40 ml of a 16 percent by weight solution of cyclooctene in benzene at 23°C was added 0.40 ml of a preformed solution of WCl$_6$, monochloroethanol and β-hydroxypropanenitrile, prepared as described for Experiment 15 in Example II, followed by 0.30 ml of an 0.20 molar solution of EADC. After 2 minutes, the polymerization was terminated with isopropanol. The yield was 69.7 percent of a solid rubbery polymer having a trans content of 31.5 percent.

EXAMPLE VIII

In the absence of solvent, 25 ml of purified cyclopentene was polymerized at 23°C by the addition of 1.0 ml of a preformed solution of WCl$_6$ and β-hydroxypropanenitrile prepared as described for Experiment 1 in Example I, followed by the addition of 0.60 ml of an 0.20 molar solution of EADC. The reaction was terminated after 120 minutes. A yield of 91.5 percent was obtained of a rubbery solid having an inherent viscosity of 3.24.

While certain representative embodiments and details have been shown for the purpose of illustrating the invention, it will be apparent to those skilled in this art that various changes and modifications may be made therein without departing from the spirit of the invention.

What is claimed is:

1. A cycloolefin metathesis process comprising polymerizing at least one unsaturated alicyclic compound selected from the group consisting of (1) unsaturated alicyclic compounds containing five carbon atoms in the ring and containing one double bond in the ring, (2) nonconjugated unsaturated alicyclic compounds containing at least seven carbon atoms in the ring and at least one double bond in the ring, and (3) polycyclic olefins and diolefins, by subjecting said alicyclic compounds or mixture thereof to polymerizations conditions in the presence of a catalyst system comprising (A) at least one transition metal salt selected from the group consisting of tungsten halides and tungsten oxyhalides, (B) at least one compound selected from the group consisting of dialkylaluminum halides, alkylaluminum sesquihalides and alkylaluminum dihalides, (C) at least one hydroxy compound of the general formula ROH wherein R is selected from the group consisting of alkyl and cycloalkyl and wherein R contains a nitrile substituted and (D) a hydroxy compound of the general formula R'OH wherein R' is selected from the group consisting of alkyl, cycloalkyl, alkoxyalkyl, haloalkyl and aryl, wherein the molar ratio of A:B:C:D lies within the range of 1:0.5–10:0.5– 3:0.5–2.

2. A process according to claim 1 wherein R contains a nitrile substituent situated on the carbon atom adjacent to that bearing the hydroxy group.

3. A process according to claim 1 wherein (A) is selected from the group consisting of $WCl_6$, $WBr_6$ and $WOCl_6$.

4. A process according to claim 1 wherein (C) is 2-hydroxypropionitrile or 2-hydroxy-1-methylpropionitrile.

5. A process according to claim 2 wherein (A) is selected from the group consisting of $WCl_6$, $WBr_6$ and $WOCl_4$ and (C) is 2-hydroxypropionitrile or 2-hydroxy-10-methylpropionitrile.

6. A process according to the previous claims wherein cyclopentene is polymerized or copolymerized.

7. A process according to claim 5 in which cyclopentene is polymerized.

* * * * *